(12) United States Patent  
Sapian

(10) Patent No.: US 9,192,451 B2
(45) Date of Patent: Nov. 24, 2015

(54) OSCILLATING BLADE FOR CUTTING PERIODONTAL LIGAMENTS AND LUXATING TOOTH ROOTS

(76) Inventor: Schubert L. Sapian, Grand Prairie, TX (US)

( * ) Notice: Subject to any disclaimer, the term of this patent is extended or adjusted under 35 U.S.C. 154(b) by 0 days.

(21) Appl. No.: 13/554,308

(22) Filed: Jul. 20, 2012

(65) Prior Publication Data

US 2014/0023988 A1  Jan. 23, 2014

(51) Int. Cl.
  *A61C 1/07*  (2006.01)
  *A61C 3/03*  (2006.01)

(52) U.S. Cl.
  CPC .......................... *A61C 3/03* (2013.01)

(58) Field of Classification Search
  CPC .......... A61C 1/07; A61C 148/08; A61C 3/12; A61C 3/14; A61C 5/026; A61B 17/320068; A61B 17/320008; A61B 5/150442; A61B 5/150458; A61B 5/150465
  USPC ......... 433/118, 119, 102, 165, 141, 143, 144, 433/145, 147, 152, 153, 215; 606/79, 606/83–85, 167, 170, 171, 172, 184, 178
  See application file for complete search history.

(56) References Cited

U.S. PATENT DOCUMENTS

| 679,693 | A | * | 7/1901 | Burkhart | B23B 51/108 408/191 |
| 3,358,826 | A | * | 12/1967 | Siegel | 206/368 |
| 4,044,468 | A | * | 8/1977 | Kahn | 433/102 |
| 5,632,746 | A | * | 5/1997 | Middleman et al. | A61B 10/02 606/170 |
| 5,941,706 | A | * | 8/1999 | Ura | 433/165 |
| 6,309,219 | B1 | * | 10/2001 | Robert | 433/144 |
| 6,726,690 | B2 | * | 4/2004 | Eckman | A61B 17/1671 606/170 |
| 7,513,722 | B2 | * | 4/2009 | Greenberg et al. | B23B 49/005 408/202 |
| 8,137,101 | B2 | * | 3/2012 | Fujii et al. | 433/75 |
| 2002/0182565 | A1 | * | 12/2002 | Senia et al. | 433/102 |
| 2006/0035196 | A1 | * | 2/2006 | Boiteux et al. | 433/82 |
| 2008/0188878 | A1 | * | 8/2008 | Young | 606/169 |
| 2009/0181342 | A1 | * | 7/2009 | Chien | 433/119 |
| 2011/0300506 | A1 | * | 12/2011 | Curry et al. | 433/75 |

* cited by examiner

*Primary Examiner* — Yogesh Patel
(74) *Attorney, Agent, or Firm* — Law Offices of Morland C. Fischer

(57) ABSTRACT

A cutting blade having a pair of razor-sharp cutting edges and adapted to be oscillated back and forth in order to cut through the periodontal ligaments which surround a tooth root of a patient during dental surgery so that the root or a portion of a tooth root can be removed from the patient's jawbone. The cutting blade has a connecting shaft at one end by which the blade can be coupled to the driver head of an oscillating dental handpiece. Located opposite the connecting shaft is a cutting end having a tissue debris transfer canal at the bottom or inside thereof and a smooth tissue gliding surface at the top or outside. A positioning collar surrounds the connecting shaft to provide to the oral surgeon a visual indication of the alignment of the pair of cutting edges of the cutting blade relative to the tissue to be cut.

9 Claims, 6 Drawing Sheets

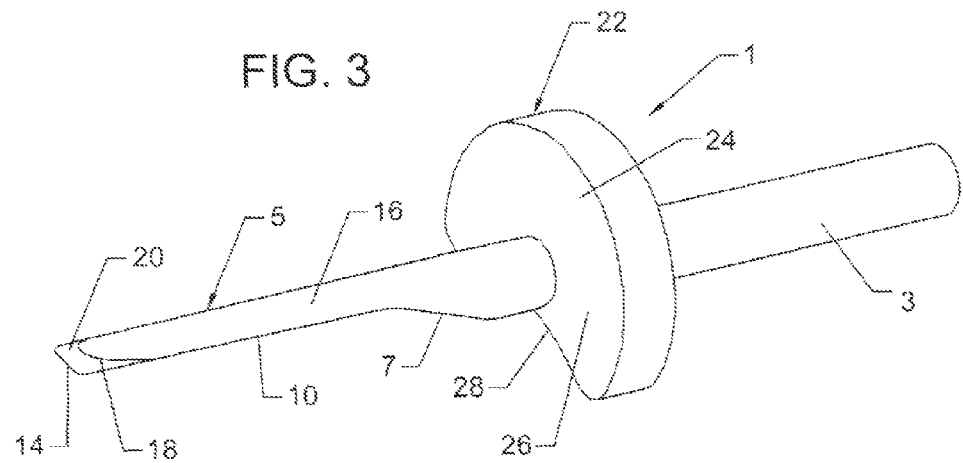
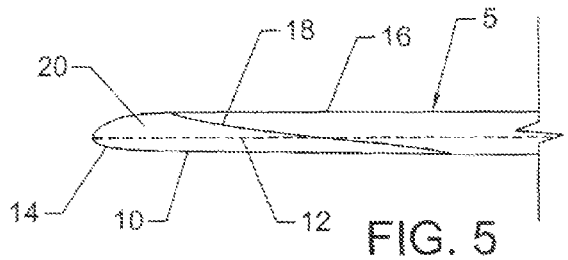
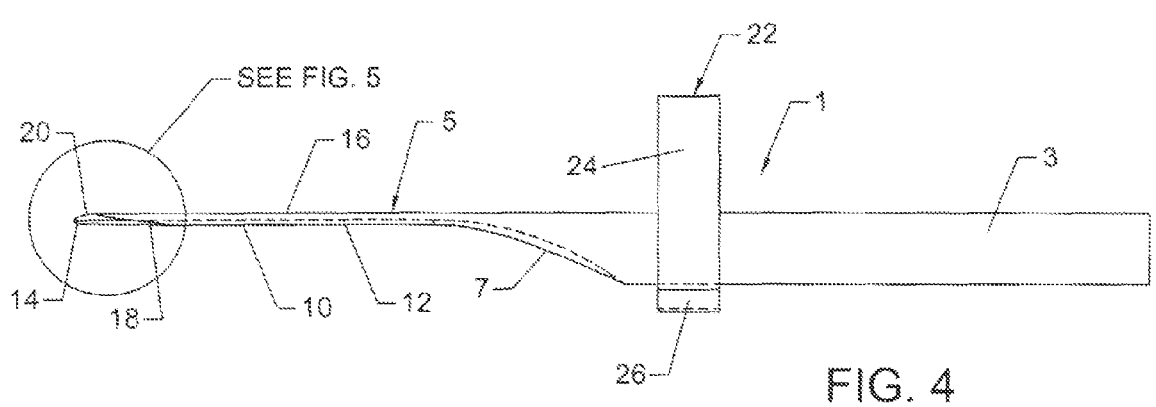

OSCILLATING BLADE FOR CUTTING PERIODONTAL LIGAMENTS AND LUXATING TOOTH ROOTS

BACKGROUND OF THE INVENTION

1. Field of the Invention

This invention relates to a longitudinally-curved cutting blade adapted to be oscillated back and forth around a tooth root and having a pair of razor-sharp cutting edges that cut through the periodontal ligaments that hold a tooth within the socket of the jawbone. By cutting most of the periodontal ligaments with the disclosed cutting blade, the tooth may be extracted with much less force and with less risk of damage to surrounding bone or other soft tissues.

2. Background Art

The need for extracting a tooth arises from a variety of circumstances. Gross decay or trauma may compromise the integrity and function of the crown or the root of a tooth to the point that the tooth must be removed. Wisdom teeth have no functional utility for most patients and can cause a variety of problems that make it advisable to extract them. Such problems can include crowding and distorting the placement of functional teeth causing pain and, because wisdom teeth are hard to reach and clean, increasing the likelihood of oral infection and decay. Traditionally, tooth extraction has been performed using a combination of physical forces that create risk of damaging the bone surrounding the tooth and the adjacent gum tissue. Such techniques include rocking the tooth back and forth using forceps, leveraging the tooth using elevators to create pressure against the surrounding bone or, in some extreme cases, extracting a tooth or root by cutting into the bone or even using a chisel and hammer. In general, all of these methods pose the risk of damaging the bone socket surrounding the tooth and the gum tissue adjacent to the tooth. This damage increases patient discomfort, requires additional time to heal, and increases the risk of infection. Moreover, in many cases, when the bone surrounding the tooth has been damaged, such damage becomes permanent because of bone resorption. For all of the above reasons, a cutting blade is desirable that will minimize the force required to extract a tooth, minimize damage to surrounding bone and gum tissue, and be compatible with modern dental equipment utilizing high speed power equipment.

SUMMARY OF THE INVENTION

According to a preferred embodiment, the cutting blade includes a cylindrical connecting shaft at one end and a cutting end at the opposite end. A sloping face extends between the connecting shaft and the cutting end for providing a smooth surface that will slide around the crown of the tooth during surgery. The cutting end has a pair of razor-sharp cutting edges. The connecting shaft is sized and shaped for receipt by the driver head carried by the arm of a conventional oscillating dental handpiece by which the cutting end is oscillated back and forth to cause the cutting edges of the blade to slice through the patient's tissue (e.g., particularly the periodontal ligaments which lie between the patient's jawbone and the root to be extracted). The top of the cutting end of the blade has a smooth curved tissue gliding surface, and the bottom of the cutting blade has a concave tissue debris transfer canal formed therein so that tissue cut by the blade during surgery can be efficiently removed from the cutting site.

A positioning collar surrounds the connecting shaft of the cutting blade. The positioning collar preferably has a round disk-like top and an arc or similar depression formed in the bottom and lying opposite the top. The longitudinal axes of the arc of the positioning collar and the cutting end of the cutting blade are co-planar so that the orientation of the arc provides the surgeon with a visual indication of the orientation of the cutting edges of the cutting blade with respect to the tissue to be cut.

A beveled recess is formed in the tissue gliding surface at the top of the cutting end of the cutting blade. The recess is located between a tissue slicing tip at the front of the cutting blade and a round nose that is spaced rearwardly from the tip. During oscillation of the cutting end, the tissue slicing tip cuts easily through the patient's periodontal ligaments while the round nose located behind the tip slides around and prevents damage to the patient's gum and bone during surgery by limiting the penetration of the tip therewithin.

BRIEF DESCRIPTION OF THE DRAWINGS

FIG. 3 is a perspective view showing the top and the first side of the double-edged cutting blade of FIG. 1;

FIG. 4 is a side view of the cutting blade of FIG. 1;

FIG. 5 is an enlarged detail of a tissue slicing tip of the cutting blade taken from FIG. 4;

DESCRIPTION OF THE PREFERRED EMBODIMENT

Figure 1:
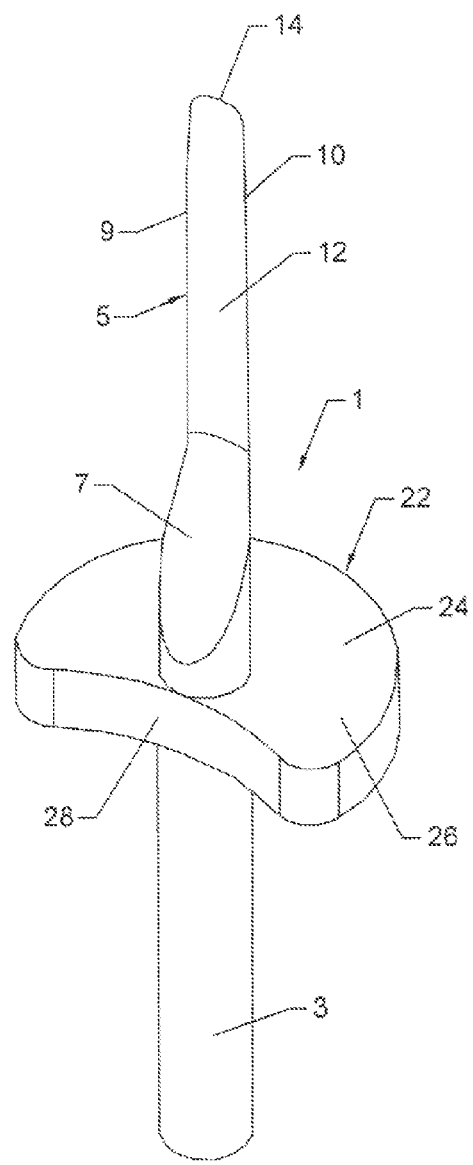
FIG. 1 is a perspective view showing the bottom and a first side of a double-edged oscillating cutting blade for use during oral surgery according to a preferred embodiment of this invention.
Figure 2:
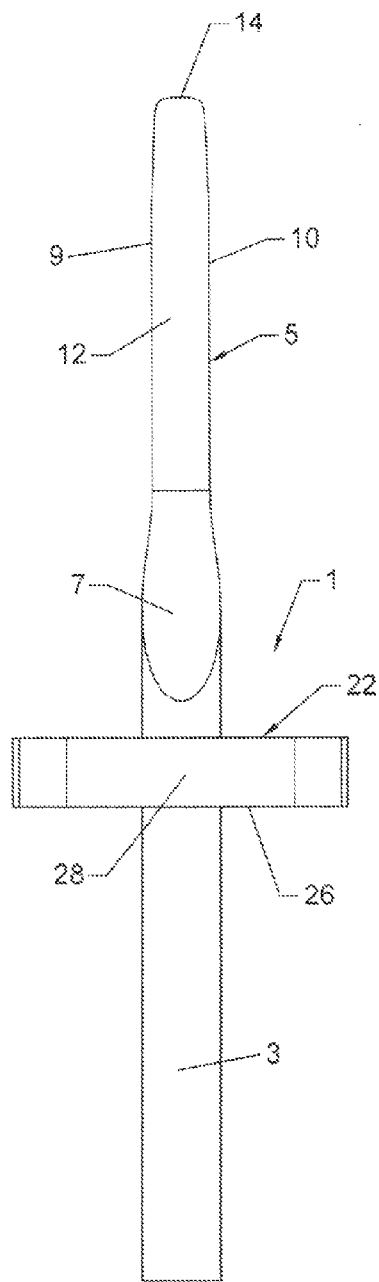
FIG. 2 is a bottom view of the double-edged cutting blade of FIG. 1.

The double-edged cutting blade which forms the present invention is disclosed while referring to the drawings. As will be described while referring to FIG. 6, the cutting blade is adapted to be removably coupled to a conventional oscillating driver head of a slow speed oscillating dental hand piece (sometimes known as a right angle hand piece) or of a battery-operated cordless device at which the cutting blade is oscillated so as to be able to cut through the periodontal tissue of a dental patient undergoing oral surgery. It is to be recognized that the cutting blade of this invention can be used on both human and animal patients. As will be described in greater detail hereinafter, the cutting blade has a pair of razor sharp cutting edges. The cutting blade is subjected to an oscillatory or reciprocal (i.e., back and forth) movement during which the pair of cutting edges slice through the patient's tissue, particularly the tissue surrounding a tooth root to be excised. By way of example, the cutting blade of this invention is especially applicable for cutting the periodontal ligaments lying between the patient's jaw bone and the root during oral surgery for the extraction of the root or root tip. By virtue of the reciprocating/oscillating movement of the blade upon the periodontal ligaments and the tooth root, the tooth to be extracted is micro-luxated resulting in a reduction of the extraction force necessary to extract the tooth.

The details for a double-edge cutting blade 1 according to a first preferred embodiment are disclosed while referring concurrently to FIGS. 1-6 of the drawings. The cutting blade 1 is preferably manufactured from stainless steel or any other suitable flexible or non-flexible metallic or non-metallic material (including, but not limited to, ceramic, plastic or carbon fiber). The cutting blade 1 includes a cylindrical connecting shaft 3 at the rear end thereof to be coupled to the driver head 32 that is carried by an arm 34 of an oscillating dental handpiece 30 (of FIG. 6). An oscillating driving force generated by the driver head 32 is transferred to the cutting blade 1 at the cylindrical driving shaft 3 thereof for causing the blade to correspondingly oscillate back and forth through an angle of about 30 degrees in order to cut through the patient's periodontal ligamental tissue. For the embodiment shown in FIGS. 1-6, the cylindrical shaft 3 of cutting blade 1 is either solid or hollow.

Located opposite the connecting shaft 3 at the front of the cutting blade 1 is a cutting end 5. The cutting end 5 is co-extensively joined to the connecting shaft 3 by way of a sloping face 7 that slopes downwardly towards the cutting end. The downwardly-sloping face 7 is preferably beveled to enable the cutting blade 1 to more easily slide around the crown of the tooth during surgery. As is best shown in FIGS. 3 and 4, the cutting end 5 of cutting blade 1 has an arcuate (e.g., curved) configuration. The cutting end 5 and the sloping face 7 of the cutting blade 1 may be formed by machining (e.g., grinding) one end of a solid rod, such the cylindrical connecting shall 3 lies opposite the cutting end 5 with the sloping face 7 located therebetween. The opposite cutting edges 9 and 10 of the cutting end 5 are thinned and razor sharpened so that the cutting blade 1 is capable of cutting through the patient's periodontal ligaments during each stroke as the blade oscillates back and forth and micro-luxates the tooth root to be extracted.

The bottom or inside of the cutting end 5 of the cutting blade 1 is machined to have a concave surgical tissue debris transfer canal 12. The tissue debris transfer canal 12 is preferably a channel that runs longitudinally from the sloping face 7 to a tissue slicing tip 14. Like the sharp cutting edges 9 and 10 of the cutting end 5, the tissue slicing tip 14 is thinned and razor sharpened to enable the cutting end 5 to penetrate and slice through the periodontal ligament tissue to be cut as the blade 1 is oscillated.

The top or outside of the cutting end 5 at the front of cutting blade 1 has a smooth, curved tissue gliding surface 16 that lies opposite the tissue debris transfer canal 12. The tissue gliding surface 16 has at a round protruding nose 18 (best shown in FIG. 3) that lies behind and is spaced rearwardly from the tissue slicing tip 14. A recess 20 (best shown in FIGS. 3-5) is established in the tissue gliding surface 16 of the cutting end 5 so as to lie between the cutting edges 9 and 10 and extend from the nose 18 to the tissue slicing tip 14. The recess 20 is preferably beveled in the tissue gliding surface 16 by means of a conventional chamfering process. Thus, the thickness of the cutting end 5 of the doubled-edged cutting blade 1 is less at the recess 20 than at the nose 18.

The curved tissue gliding surface 16 at the top of the cutting end 5 is shaped to advantageously prevent damage to the patient's gingival or soft tissue (i.e., the gums) during surgery. That is, the tissue gliding surface 16 slides smoothly through the patient's tissue once the doubled-edged cutting blade 1 enters the periodontal ligamental (PDL) space. In addition, the curved tissue gliding surface 16 reduces drag which limits damage to and loss of the cortical bone or hard tissue of the patient so as to speed the time for healing following surgery.

The concave tissue debris transfer canal 12 at the bottom of the cutting end 5 is shaped to create a smooth flow path to permit an efficient removal of the patient's soft and hard tissues that are cut away during the process of excising of the root as the doubled-edged cutting blade 1 moves through the PDL space. The ability and speed of the blade 1 to slice through the periodontal ligaments is maximized by virtue of the opposite cutting edges 9 and 10 of cutting end 5. Since the PDL space is typically about 0.13 mm to 0.40 mm wide, the cutting end 5 of the double-edged cutting blade 1 must be thinner than 0.40 mm to avoid damaging the patient's jaw bone. The cutting edges 9 and 10 of the cutting end 5 are razor sharp to easily glide into the PDL space as the blade 1 is oscillated by the oscillating driver head 32 of the oscillating dental hand piece 30 of FIG. 6.

The beveled recess 20 formed in the top of the cutting end 5 of the doubled-edged cutting blade 1 between the tissue slicing tip 14 and the protruding nose 18 at the tissue gliding surface 16 prevents the tip from cutting and damaging the hard and soft tissues which surround the tooth root as the blade 1 cuts through the PDL towards the root. To this end, the cutting blade 1 is oriented by the surgeon such that the tissue gliding surface 16 at the top of cutting end 5 faces the bone and is turned away from the tooth root.

A positioning collar 22 is slid into engagement with the double-edged cutting blade 1 or machined with the blade as a single piece so as to surround the cylindrical connecting shaft 3. A cylindrical opening (not shown) through the positioning collar 22 is sized to receive the connecting shaft 3 therethrough. The positioning collar 22 has a round disk-like top portion 24 and either an arc 28 (or similar depression or marking) as shown or a flat (not shown) formed in the bottom portion 26 opposite the round top portion 24. The shape of the round top portion 24 and the arc 28 or flat in the bottom portion 26 may change so long as the shape of one is visually distinguishable from the shape of the other.

Figure 6:
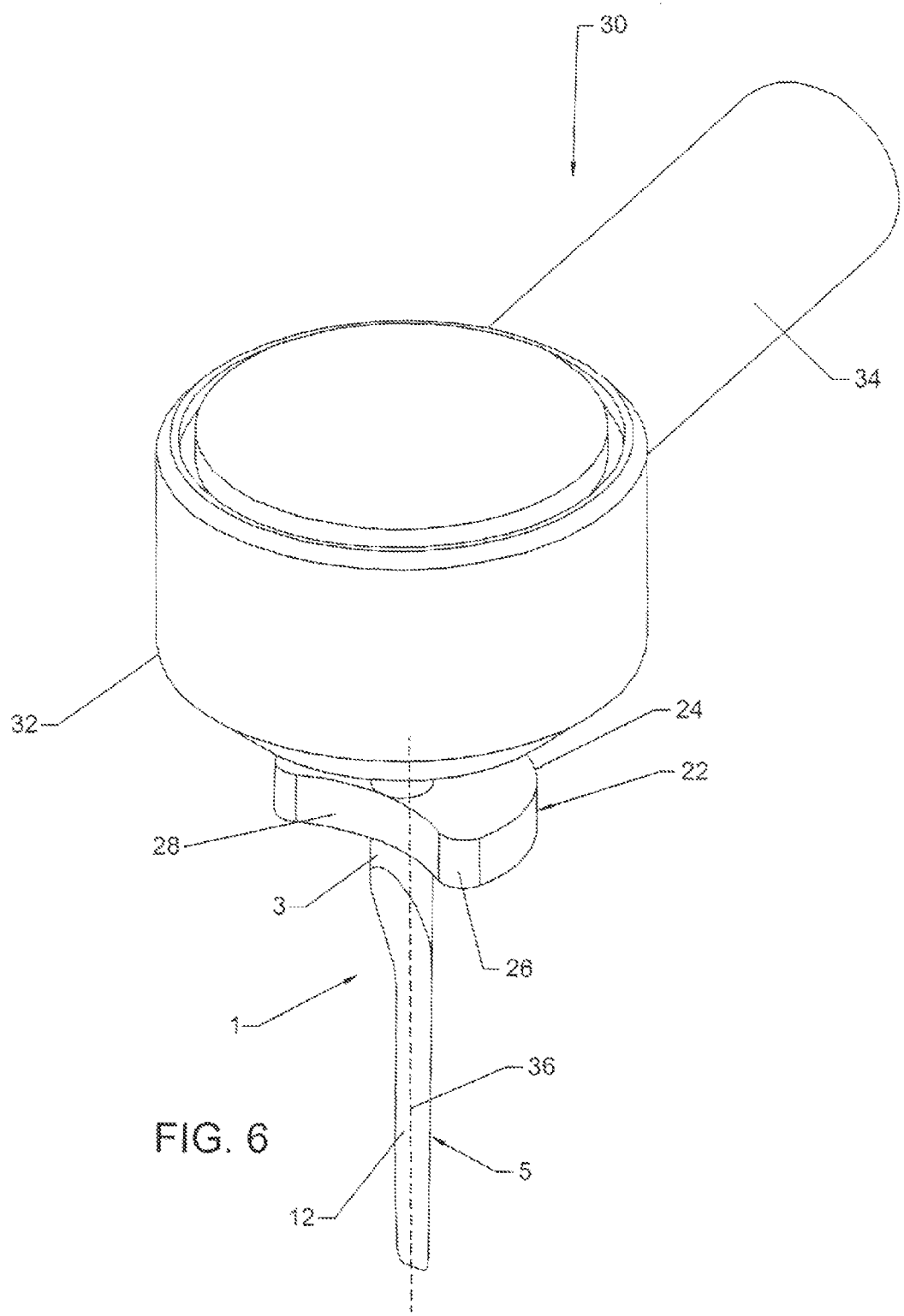
FIG. 6 shows the cutting blade of FIG. 1 connected to the driver head of a conventional oscillating dental handpiece so that the cutting blade can be oscillated back and forth for cutting through the patient's tissue.
Figure 7:
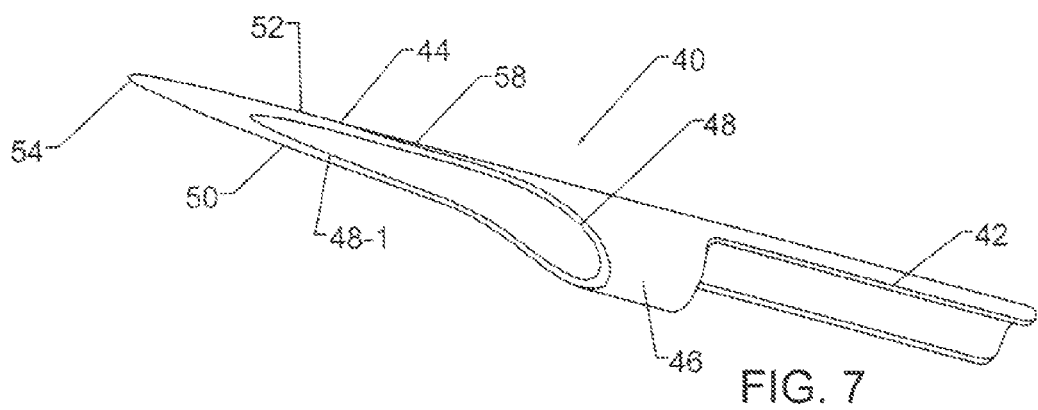
FIG. 7 is a perspective view showing the bottom and a first side of a double-edged oscillating cutting blade according to another preferred embodiment of this invention.
Figure 8:
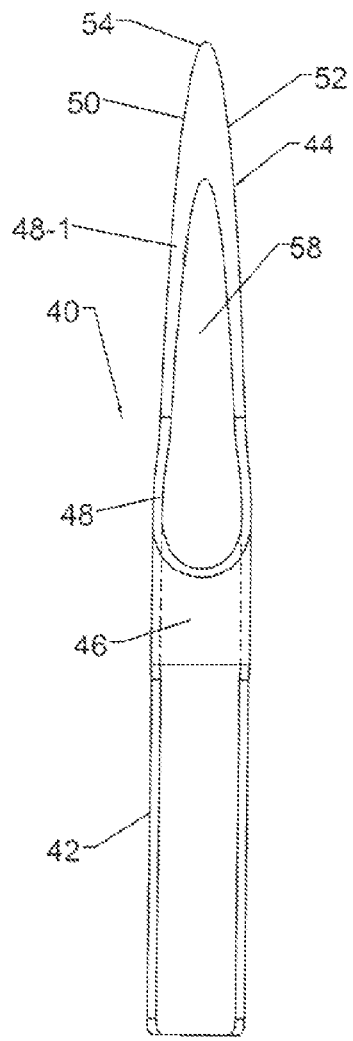
FIG. 8 is a bottom view of the cutting blade of FIG. 7.
Figure 9:
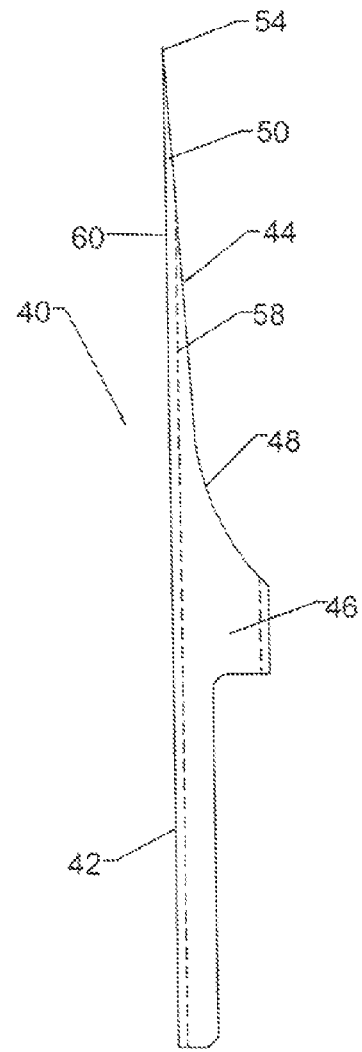
FIG. 9 is a side view of the cutting blade of FIG. 7.
Figure 10:
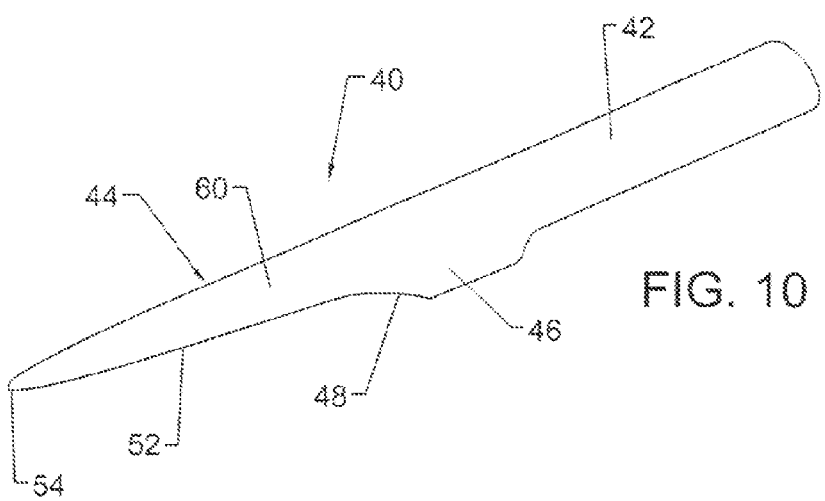
FIG. 10 is a perspective view showing the top and a first side of the cutting blade of FIG. 7.

In the embodiment shown in FIGS. 1-4, the positioning collar 22 is oriented in surrounding engagement with the cutting blade 1 so that the longitudinal axis of the arc 28 at the bottom portion 26 is co-planar with the longitudinal axis of the concave tissue debris transfer canal 12 which runs along the bottom of the cutting end 5 in the manner illustrated in FIG. 6 with respect to the plane designated by the reference numeral 36. In other words, the shape and alignment of the arc 28 of the positioning collar 22 correspond with the shape and alignment of the concave bottom of the cutting end 5. In this way, the surgeon will be visually alerted, depending upon the orientation of the arc 28 of the positioning collar 22, as to the corresponding orientation of the cutting edges 9 and 10 of the cutting end 5 as well as the tissue transfer canal 12 and the tissue gliding surface 16 which lie one above the other at the bottom and top of end 5. Thus, the double-edged cutting blade 1 can be accurately positioned and manipulated relative to the patient's tissue so as to be moved into the periodontal ligament space while causing minimal tissue and bone damage.

The details for a double-edged cutting blade 40 according to a second preferred embodiment are disclosed while referring concurrently to FIGS. 7-10 of the drawings. The cutting blade 40 is adapted to be removably coupled to a battery-powered cordless oscillating device (not shown) at which the cutting blade is oscillated back and forth so as to be able to slice the periodontal ligaments which secure the root of a tooth to the jaw bone of a dental patient undergoing oral surgery for the extraction of the root. The cutting blade 40 is especially useful for surgery in the field or outside a traditional dental office when an electrically-driven dental hand piece is not available.

Located at the rear of the double-edged cutting blade 40 is a hollow semi-cylindrical connecting arm 42 by which the blade 40 is detachably connected to the cordless oscillating device. The connecting arm 42 is shaped in order to be mated to and held against a complementary coupler (also not shown) of the oscillating device. Located at the front of the cutting blade 40 is an arcuate (i.e., curved) cutting end 44. The cutting end 44 is preferably manufactured from a flexible metallic or non-metallic material. Located between the connecting arm 42 and the cutting end 44 of blade 40 is a hollow tubular intermediate sleeve 46.

The hollow intermediate sleeve 46 has a sloping face 48 which slopes downwardly towards and extends to the beginning of the cutting end 44. The downwardly-sloping face 48 of sleeve 46 is preferably beveled to enable the cutting blade 40 to more easily slide around the crown of the tooth during surgery. The opposite edges 50 and 52 of the cutting end 44 of the double-edged cutting blade 40 are thinned and razor sharpened so that the cutting blade 40 is capable of cutting through the PDL space during each stroke as the blade oscillates back and forth. The cutting end 44 of the double-edged cutting blade 40 is tapered inwardly from the intermediate sleeve 46 to a tissue slicing tip 54. The tissue slicing tip 54 can be pointed (as shown), round, straight or saw-toothed.

With respect to the tapered cutting end 44 shown in FIGS. 7-10 that terminates at the pointed tip 54, it may be appreciated that the narrowest location along the cutting end 44 is the tip 54. The pointed tip 54 facilitates a precise placement of the cutting blade 40 during surgery, especially interproximally between the teeth. Such a pointed tip 54 also allows the accurate creation of a purchase point. On the other hand, a rounded tip (not shown) has more surface area which enables a higher cutting speed and efficiency.

In this same regard, the cutting end 44 is widest and strongest adjacent the hollow intermediate sleeve 46 where most of the cutting takes place through the PDL. The relatively wide portion of the cutting end 44 is also responsible for microluxation which vibrates or moves the tooth root and thereby stimulates collagenase formation. Such formation breaks down the collagen fibers of the PDL for causing water to be released from the collagen.

Like the cutting blade 1 of FIGS. 1-5, the cutting end 44 of the double-edged cutting blade 40 of FIGS. 7-10 has a surgical tissue debris transfer canal 58 formed at the inside or bottom and a smooth tissue gliding surface 60 at the outside or top. The surgical debris transfer canal 5S has a concave configuration that runs longitudinally between the intermediate sleeve 46 and the tissue slicing tip 54 at the front of cutting end 44. The debris transfer canal 58 lies between the opposite cutting edges 50 and 52 of cutting end 44 and is surrounded by an extension 48-1 of the bevel of the sloping face 48 of the intermediate sleeve 46. The surgical debris transfer canal 58 creates a continuous flow path or channel with the hollow tubular intermediate sleeve 46 to permit an efficient removal of the patient's soft and hard tissues that are cut away during the excision of the tooth root.

The smooth outside tissue gliding surface 60 at the top of the cutting end 44 is curved to advantageously prevent damage to the patient's gingival soft tissue during surgery. The curved tissue gliding surface 60 also enables the cutting blade 40 to slide smoothly through the PDL space with minimal drag, whereby damage to and loss of the hard tissue and cortical bone is minimized.

Figure 11:
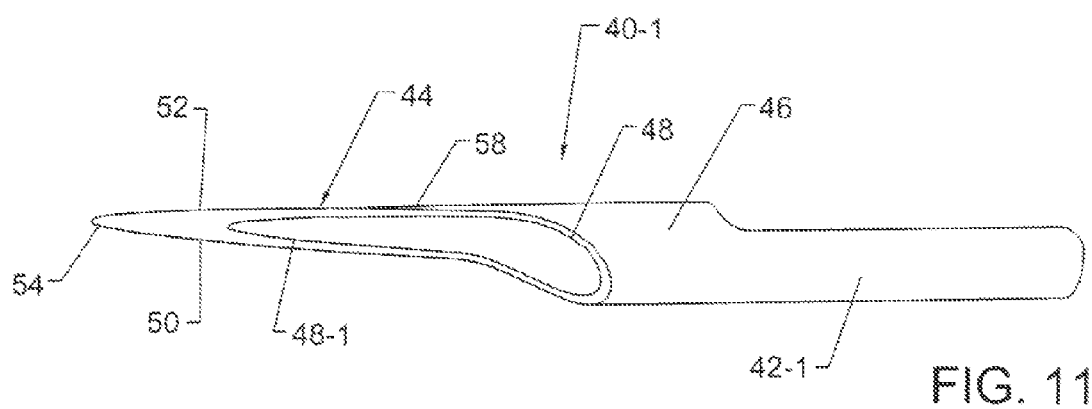
FIG. 11 is a perspective view showing the bottom and a first side of a double-edged oscillating cutting blade according to yet another preferred embodiment of this invention.
Figure 12:
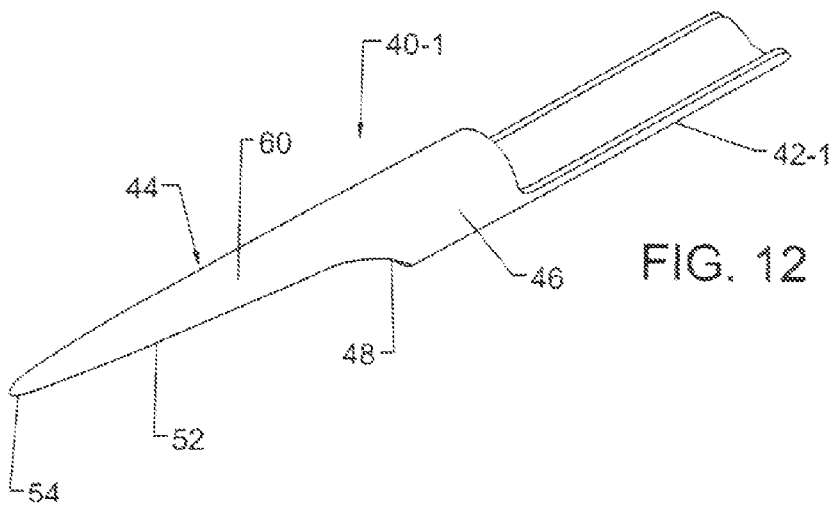
FIG. 12 is a perspective view showing the top and the first side of the cutting blade of FIG. 11.

For the double-edged cutting blade 40 shown in FIGS. 7-10, the hollow semi-cylindrical connecting arm 42 and the cutting end 44 are axially aligned and located along the top of cutting blade 40. In FIGS. 11 and 12 of the drawings, a modified double-edged cutting blade 40-1 is shown where the hollow semi-cylindrical connecting arm 42-1 is located along the bottom of blade 40-1, and the cutting end 44 is located oppositely and along the top of blade 40-1. Such a modified cutting blade 40-1 may be required depending upon the manner in which the connecting arm 42-1 is coupled to the cordless oscillating device. Identical reference numerals have been used to designate identical features of the double-edged cutting blades 40 and 40-1 of FIGS. 7-10 and 11-12.

Figure 13:
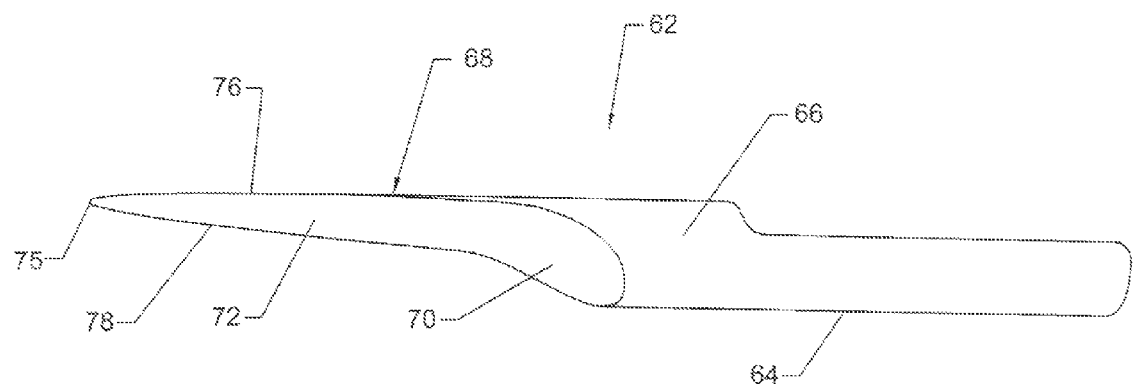
FIG. 13 is a perspective view showing the bottom and a first side of a double-edged oscillating cutting blade according to a further preferred embodiment of this invention.
Figure 14:
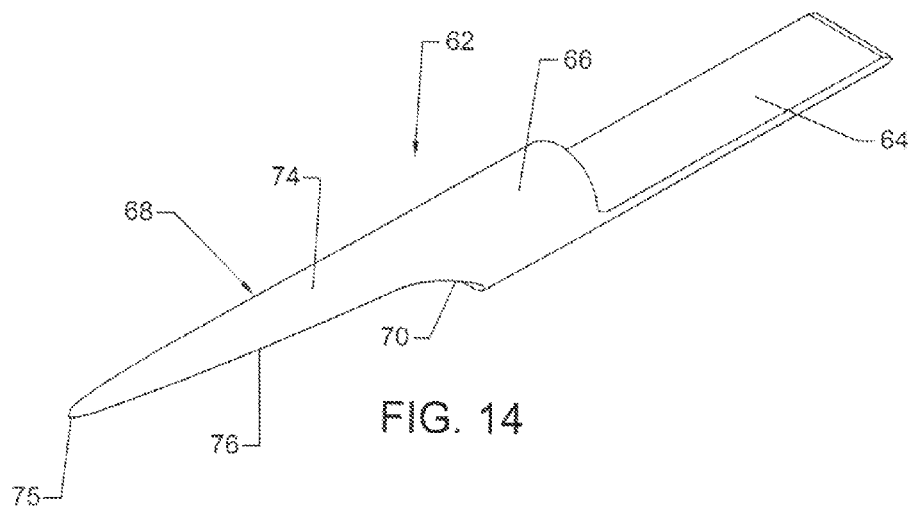
FIG. 14 is a perspective view showing the top and the first side of the cutting blade of FIG. 13.

FIGS. 13 and 14 of the drawings show a doubled-edged cutting blade 62 having some of the same features as the cutting blades 40 and 40-1 of FIGS. 7-12. Like the cutting blades 40 and 40-1, the double-edged cutting blade 62 is adapted to be detachably connected to a battery-powered cordless oscillating device that is capable of applying a reciprocating back and forth movement (perpendicular to the longitudinal axis of the blade) to the blade 62 for cutting through the hard and soft tissues of a patient undergoing oral surgery.

Unlike the cutting blades 40 and 40-1, the blade 62 of FIGS. 13 and 14 has a solid semi-cylindrical connecting arm 64 at the rear thereof. A solid intermediate joint 66 is coextensively connected between connecting arm 64 and a cutting end 68 at the front of the cutting blade 62. The solid joint 66 has a sloping face 70 which is preferably beveled. The bottom of the cutting end 68 of cutting blade 62 includes a flat inside surface 72, and the top of cutting end 68 includes a smooth, curved outside tissue gliding surface 74. The inside surface 72 at the bottom of cutting end 68 may also be concave to establish a surgical debris transfer canal like those previously described. The cutting end 68 at the front of blade 62 terminates at a sharp pointed tissue-slicing tip 75. The opposite edges 76 and 78 of the cutting end 68 are thinned and razor sharpened so as to cut through the PDL as the cutting blade 62 is oscillated back and forth. In the case of the cutting blade 62, the connecting arm 64 is located along the bottom of blade 62, and the cutting end 68 is located oppositely and along the top of blade 62. As with the cutting blade 40 shown in FIGS. 7-10, the cutting blade 62 of FIGS. 13 and 14 can be modified such that the connecting arm 64 and the cutting end 68 thereof are axially aligned and located along the top of the blade 62.

The invention claimed is:

1. A combination comprising:
   force-generating means for generating an oscillating driving force; and
   a cutting blade for cutting through human or animal periodontal ligaments (PDL) around the root of a tooth so that the root can be extracted, said cutting blade including:
   a cutting end portion having first and opposite cutting edges extending longitudinally along opposite sides thereof and a longitudinal axis running continuously along said cutting end portion between said longitudinally-extending cutting edges, a connecting end portion attached to said force-generating means so that said cutting end portion is responsive to the oscillating driving force generated by said force-generating means, whereby said cutting end portion oscillates in opposite directions through an angle greater than zero for cutting through the PDL, and a cutting end portion position indicator including a disk surrounding said cutting blade and having a depression formed in a single side thereof, said depression having a longitudinal axis that extends in the same direction and lies in the same vertical plane as the longitudinal axis of said cutting end portion such that the longitudinal axis of said depression is aligned with the longitudinal axis of said cutting end portion so as to run parallel to and provide a visual indication of the alignment of the first and opposite longitudinally-extending cutting edges of said cutting end portion with respect to the PDL being cut by said cutting edge, wherein the cutting end portion of said cutting blade has a concave tissue debris transfer canal formed therein and along which tissue cut by the first and opposite longitudinally-extending cutting edges of said cutting end portion is removed from said cutting end, said concave tissue debris transfer channel running along the longitudinal axis of the cutting end portion of said cutting blade and extending continuously along said cutting end portion between said longitudinally-extending cutting edges thereof, such that the longitudinal axis of the depression formed in the disk of said cutting end position indicator and the longitudinal axis of the concave channel of said tissue debris channel extend in the same direction and lie in the same vertical plane as the longitudinal axis of said cutting end portion.

2. The combination recited in claim 1, wherein the depression formed in the disk of said cutting end portion position indicator is a concave depression.

3. The combination recited in claim 1, wherein the disk of said cutting end portion position indicator surrounds at least some of the connecting end of said cutting blade.

4. The combination recited in claim 1, wherein said cutting blade also includes a face that slopes towards said cutting end portion and lies between said cutting end portion and said connecting end portion thereof.

5. The combination recited in claim 1, wherein said cutting blade also includes a tip located at the front thereof and extending between the longitudinally-extending cutting edges of said cutting end portion to slice through the PDL being cut, a nose located on said cutting end portion and spaced behind said tip, and a recess formed in said cutting end portion and lying between said tip and said nose, such that said cutting end portion is thinner at said recess than at said nose.

6. The combination recited in claim 5, wherein the nose located on the cutting end portion of said cutting blade is round.

7. The combination recited in claim 1, wherein the connecting end portion of said cutting blade has a flat portion so as to be received by and attached to said force-generating means.

8. The combination recited in claim 1, wherein the connecting end portion of said cutting blade is semi-cylindrical so as to be received by and attached to said force-generating means.

9. The combination recited in claim 1, wherein said cutting blade also includes a hollow sleeve located between said connecting end portion and said cutting end portion thereof, said hollow sleeve having a face that slopes towards said cutting end portion.

* * * * *